(12) United States Patent
Katsumoto et al.

(10) Patent No.: US 11,530,975 B2
(45) Date of Patent: Dec. 20, 2022

(54) CONTROL DEVICE, MICROPARTICLE SORTING DEVICE AND MICROPARTICLE SORTING SYSTEM USING CONTROL DEVICE, AND CONTROL METHOD

(71) Applicant: SONY CORPORATION, Tokyo (JP)

(72) Inventors: Yoichi Katsumoto, Tokyo (JP); Marcaurele Brun, Tokyo (JP); Kazuya Takahashi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 17/250,745

(22) PCT Filed: Aug. 19, 2019

(86) PCT No.: PCT/JP2019/032211
§ 371 (c)(1),
(2) Date: Feb. 26, 2021

(87) PCT Pub. No.: WO2020/054317
PCT Pub. Date: Mar. 19, 2020

(65) Prior Publication Data
US 2021/0349002 A1    Nov. 11, 2021

(30) Foreign Application Priority Data

Sep. 10, 2018 (JP) ............... JP2018-168712

(51) Int. Cl.
*G01N 15/10* (2006.01)
*C12M 1/00* (2006.01)
*G01N 15/14* (2006.01)

(52) U.S. Cl.
CPC . *G01N 15/1056* (2013.01); *G01N 2015/1081* (2013.01)

(58) Field of Classification Search
CPC .......... G01N 15/1056; G01N 15/1459; G01N 15/1404; G01N 2015/1081;
(Continued)

(56) References Cited

U.S. PATENT DOCUMENTS 4,325,483 A * 4/1982 Lombardo ......... G01N 15/1404
209/579
4,538,733 A * 9/1985 Hoffman ............ G01N 15/1404
209/579
(Continued)

FOREIGN PATENT DOCUMENTS

CN    102753955 A * 10/2012 ........ B01L 3/502761
CN    105143851 A    12/2015
(Continued)

OTHER PUBLICATIONS

International Search Report and Written Opinion of PCT Application No. PCT/JP2019/032211, dated Nov. 5, 2019, 08 pages of ISRWO.

*Primary Examiner* — Gene O Crawford
*Assistant Examiner* — Muhammad Awais
(74) *Attorney, Agent, or Firm* — Chip Law Group

(57) ABSTRACT

To provide a technology of efficiently and effectively sorting microparticles to be sorted from a sample solution. The present technology provides a control device being a device that controls a processing condition when sorting microparticles from a sample liquid flowing through a flow path, the control device provided with a control unit that controls a sorting processing condition on the basis of a content of microparticles to be sorted in the sample liquid. In the control device according to the present technology, the control unit may control the sorting processing condition on
(Continued)

the basis of a surviving rate and/or an activation rate of biological particles to be sorted with respect to the sorting processing condition.

8 Claims, 8 Drawing Sheets

(58) Field of Classification Search
CPC ... G01N 2015/1087; G01N 2015/1093; G01N 2015/1006; G01N 2015/1481; G01N 2015/149; C12M 47/04
USPC .......................................................... 209/577
See application file for complete search history.

(56) References Cited

U.S. PATENT DOCUMENTS

| | | | | |
|---|---|---|---|---|
| 6,809,804 B1* | 10/2004 | Yount | ................... | G06K 9/6218 |
| | | | | 356/73 |
| 9,267,873 B2* | 2/2016 | Kery | ................... | G01N 15/1031 |
| 2005/0227362 A1* | 10/2005 | Lary | ................... | G01N 15/1404 |
| | | | | 436/63 |
| 2013/0177973 A1* | 7/2013 | Kondo | ............... | G01N 15/1459 |
| | | | | 435/288.7 |
| 2013/0256136 A1* | 10/2013 | Muraki | ................... | B03C 7/003 |
| | | | | 204/555 |
| 2014/0306122 A1* | 10/2014 | Norton | ................. | G05D 7/0617 |
| | | | | 250/428 |
| 2015/0177121 A1* | 6/2015 | Takahashi | ............. | G01N 15/14 |
| | | | | 209/577 |
| 2017/0248515 A1* | 8/2017 | Duckett, Jr. | ........... | G01N 21/05 |
| 2018/0298324 A1 | 10/2018 | Takeda et al. | | |

FOREIGN PATENT DOCUMENTS

| | | | | |
|---|---|---|---|---|
| CN | 107532990 | A | | 1/2018 |
| CN | 208488366 | U | | 2/2019 |
| EP | 2984468 | A1 | | 2/2016 |
| JP | 2005-538727 | A | | 12/2005 |
| JP | 2005538727 | A | * | 12/2005 |
| JP | 2008164580 | A | * | 7/2008 |
| JP | 2009-100698 | A | | 5/2009 |
| JP | 2009100698 | A | * | 5/2009 ........ B01L 3/502738 |
| JP | 2008-164580 | B2 | | 7/2012 |
| JP | 2013-15357 | A | | 1/2013 |
| JP | 2016-521362 | A | | 7/2016 |
| KR | 20180058052 | A | * | 5/2018 |
| WO | 2014/169231 | A1 | | 10/2014 |
| WO | WO-2015122160 | A1 | * | 8/2015 ............ B01L 3/0268 |
| WO | 2016/081168 | A1 | | 5/2016 |
| WO | 2016/182034 | A1 | | 11/2016 |
| WO | WO-2016182034 | A1 | * | 11/2016 ........ B01L 3/502761 |
| WO | WO-2018097950 | A1 | * | 5/2018 ............ C12M 23/12 |

* cited by examiner

CONTROL DEVICE, MICROPARTICLE SORTING DEVICE AND MICROPARTICLE SORTING SYSTEM USING CONTROL DEVICE, AND CONTROL METHOD

CROSS REFERENCE TO RELATED APPLICATIONS

This application is a U.S. National Phase of International Patent Application No. PCT/JP2019/032211 filed on Aug. 19, 2019, which claims priority benefit of Japanese Patent Application No. JP 2018-168712 filed in the Japan Patent Office on Sep. 10, 2018. Each of the above-referenced applications is hereby incorporated herein by reference in its entirety.

TECHNICAL FIELD

The present technology relates to a device that controls a processing condition when sorting microparticles. In detail, this relates to a control device that controls a processing condition when sorting microparticles from a sample liquid flowing through a flow path, a microparticle sorting device and a microparticle sorting system using the control device, a control method, and a control program.

BACKGROUND ART

In recent years, along with development of analytical methods, a method of allowing biological microparticles such as cells and microorganisms, microparticles such as microbeads and the like to flow through a flow path, and individually measuring the microparticles and analyzing or sorting the measured microparticles at a step of flowing has been developed.

As a representative example of such a method of analyzing or sorting the microparticles, technological improvement of an analytical method referred to as flow cytometry is advancing rapidly. The flow cytometry is an analytical method of analyzing and sorting the microparticles by allowing microparticles to be analyzed to flow in a state being arrayed in fluid and irradiating the microparticles with laser light and the like to detect fluorescence and scattered light emitted from each of the microparticles.

In the analysis of the microparticles represented by the flow cytometry and the like, an optical method is often used in which the microparticles to be analyzed are irradiated with light such as a laser to detect fluorescence or scattered light emitted from the microparticles. Then, on the basis of the detected optical information, a histogram is extracted by an analytical computer and software, and analysis is performed.

For example, in a flow cytometer, a plurality of types of cells and the like contained in a sample is labeled with fluorescent dyes, and the fluorescent dyes labeled on the respective cells and the like are optically identified, so that only a specific type of cell and the like is separately recovered. The separately recovered cells and the like may be used in production of a cell preparation and the like.

Patent Documents 1 and 2 disclose a microchip-type microparticle sorting device that forms a sheath flow in a flow path formed in a microchip made by using plastic or glass, for example, to perform analysis.

The microparticle sorting device disclosed in Patent Document 1 controls a feeding direction of the sheath flow at a branch by generating bubbles by laser irradiation at the branch between an introduction flow path in which the sheath flow is formed and a branch flow path communicated with the introduction flow path. According to this microparticle sorting device, by controlling the feeding direction of the sheath flow at the branch by bubbles, it is possible to take only target microparticles into the branch flow path from the introduction flow path to sort.

Furthermore, a microfluidic system disclosed in Patent Document 2 sorts target microparticles by controlling a feeding direction of the sheath flow in a flow path branch by using an actuator. In this microfluidic system, the actuator presses a chamber connected to the branch between an introduction flow path in which the sheath flow is formed and the branch flow path communicated with the introduction flow path, and pushes out liquid in the chamber to change a feeding direction of the sheath flow.

CITATION LIST

Patent Document

Patent Document 1: Japanese Patent Application Laid-Open No. 2009-100698
Patent Document 2: Japanese Unexamined Patent Publication No. 2005-538727

SUMMARY OF THE INVENTION

Problems to be Solved by the Invention

As described above, microparticles such as cells sorted by using the microparticle sorting device are used in the production of the cell preparation and the like; however, for example, a proportion of each immunocompetent cell in peripheral blood mononuclear cell suspension varies, and there has been a problem that it is originally difficult to define an amount of effective ingredient (number of effective cells) and an amount of impurities (number of unnecessary cells) in order to produce the cell preparation for performing cell infusion therapy and the like starting from this.

Alternatively, in order to define the amount of effective ingredient, there is a method of producing an excessive amount of cells in advance, measuring a fraction of the number of effective cells contained in the produced cell suspension at a final stage, and diluting by an appropriate medium liquid amount from a measurement result to adjust the amount of cells; however, there has been a problem that it is required to excessively prepare the cell amount to be produced or a collected blood amount at a starting point.

Furthermore, in a case of sorting by using the microparticle sorting device, there has been a problem of a case where sufficient cell surviving rate or activation rate cannot be obtained because a processing time is prioritized, a case where a long work time is required and the sufficient number of acquired cells cannot be obtained because the surviving rate and activation rate are prioritized to the contrary and the like.

Therefore, a principal object of the present technology is to provide a technology of efficiently and effectively sorting microparticles to be sorted from a sample solution.

Solutions to Problems

That is, first, the present technology provides
a control device being a device that controls a processing condition when sorting microparticles from a sample liquid flowing through a flow path, the control device provided with a control unit that controls a sorting processing condition on the basis of a content of microparticles to be sorted in the sample liquid.

In the control device according to the present technology, the content may be calculated from a measurement result obtained from the sample liquid at a pre-measurement step.

In the control device according to the present technology, the sorting processing condition may be one or more conditions selected from a flow rate of the sample liquid, a sorting processing time, and a sorting processing interval.

In the control device according to the present technology, bio-related microparticles may be used as the microparticles.

In the control device according to the present technology, the control unit may control the sorting processing condition on the basis of a surviving rate and/or an activation rate of biological particles to be sorted with respect to the sorting processing condition.

In this case, the surviving rate and/or the activation rate may also be calculated from a measurement result obtained from the biological particles in the sample liquid at the pre-measurement step.

Next, the present technology provides
a microparticle sorting device provided with
a light detection unit that detects optical information obtained from a sample liquid,
a sorting unit that sorts microparticles from the sample liquid on the basis of the detected optical information, and
a control unit that controls a sorting processing condition in the sorting unit on the basis of a content of microparticles to be sorted in the sample liquid.

The present technology also provides
a microparticle sorting system provided with
a sorting device provided with
a light detection unit that detects optical information obtained from a sample liquid flowing through a flow path, and
a sorting unit that sorts microparticles from the sample liquid on the basis of the detected optical information, and
a control device provided with a control unit that controls a sorting processing condition in the sorting unit on the basis of a content of microparticles to be sorted in the sample liquid.

The present technology further provides
a control method being a method of controlling a condition of sorting microparticles from a sample liquid flowing through a flow path,
the control method provided with a control step of controlling a sorting processing condition on the basis of a content of microparticles to be sorted in the sample liquid.

The present technology also provides
a control program being a program used to control a condition of sorting microparticles from a sample liquid flowing through a flow path,
the control program for allowing a computer to realize a control function of controlling a sorting processing condition on the basis of a content of microparticles to be sorted in the sample liquid.

In the present technology, "microparticles" broadly include bio-related microparticles such as cells, microorganisms, and liposomes, synthetic particles such as latex particles, gel particles, and industrial particles or the like.

The bio-related microparticles include chromosomes forming various cells, liposomes, mitochondria, organelles (cell organelles) and the like. The cells include animal cells (such as blood cells) and plant cells. The microorganisms include bacteria such as *Escherichia coli*, viruses such as tobacco mosaic virus, fungi such as yeast and the like.

Moreover, the bio-related microparticles may also include bio-related polymers such as nucleic acids, proteins, and complexes thereof.

Furthermore, the industrial particles may be, for example, an organic or inorganic polymer material, metal or the like. The organic polymer material includes polystyrene, styrene/divinylbenzene, polymethyl methacrylate and the like. The inorganic polymer material includes glass, silica, a magnetic material and the like. The metal includes gold colloid, aluminum and the like. In general, shapes of the microparticles are generally spherical, but they may be non-spherical, and its size, mass and the like are also not especially limited.

MODE FOR CARRYING OUT THE INVENTION

Figure 1:
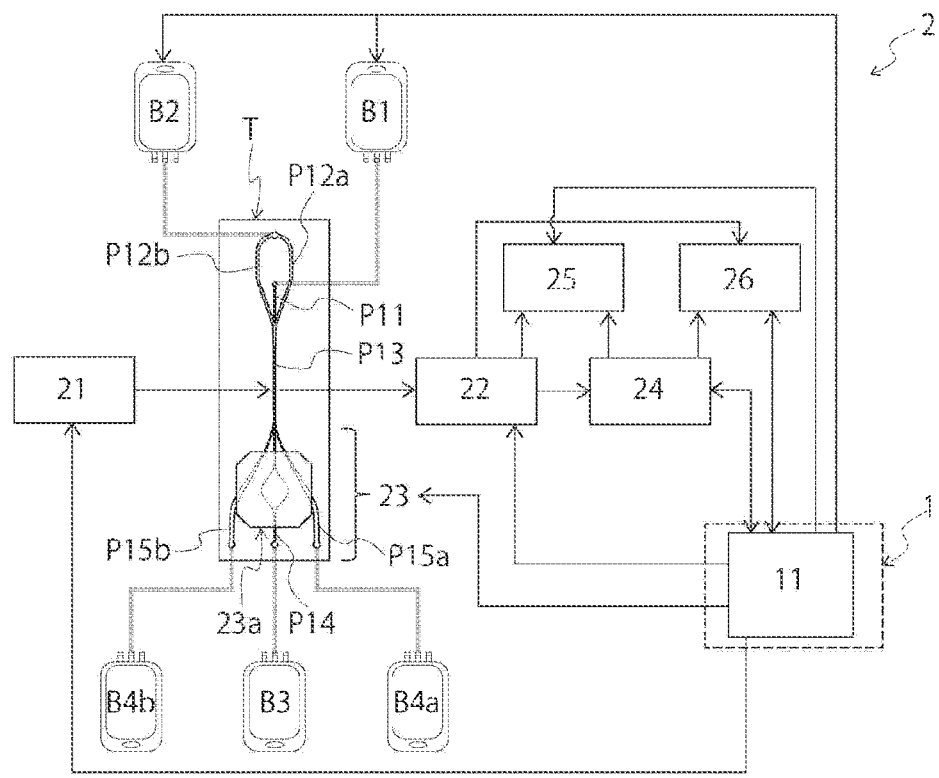
FIG. 1 is a schematic conceptual diagram schematically illustrating a first embodiment of a microparticle sorting device 2 in which a control device 1 according to the present technology may be used.

Hereinafter, a preferred mode for carrying out the present technology is described with reference to the drawings. An embodiment hereinafter described illustrates an example of a representative embodiment of the present technology, and the scope of the present technology is not narrowed by this. Note that the description is given in the following order.

1. Control device 1, microparticle sorting device 2
(1) Flow path P
(2) Light irradiation unit 21
(3) Light detection unit 22
(4) Sorting unit 23
(5) Control unit 11
(6) Analysis unit 24
(7) Storage unit 25
(8) Display unit 26
2. Microparticle sorting system 3
3. Control method, microparticle sorting method
4. Control program

1. Control Device 1, Microparticle Sorting Device 2

Figure 2:
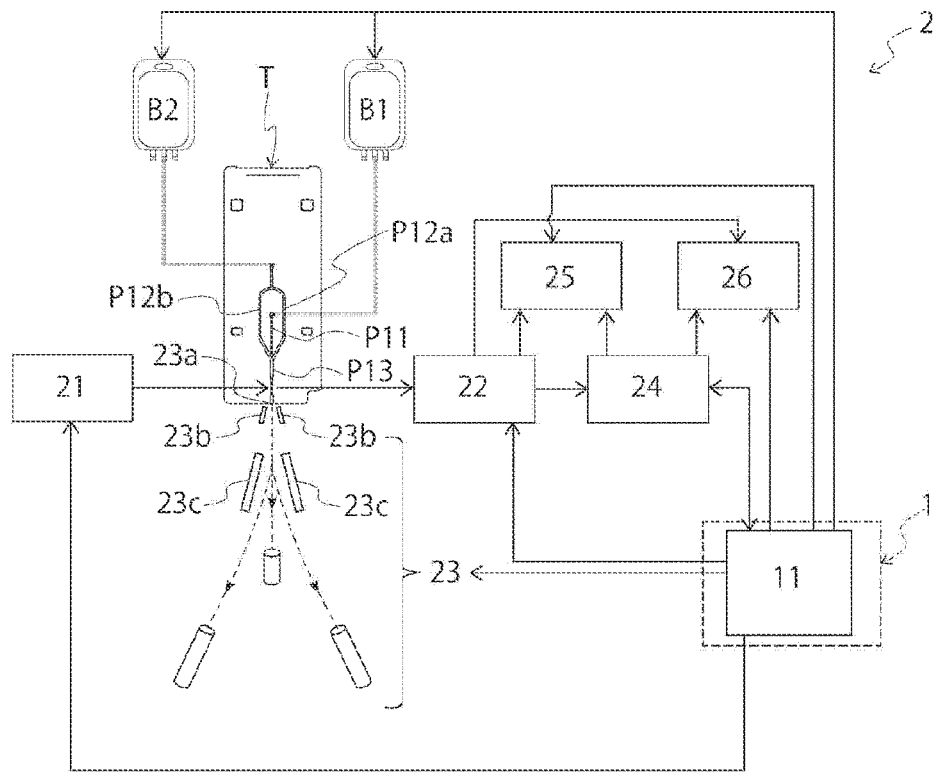
FIG. 2 is a schematic conceptual diagram schematically illustrating a second embodiment of the microparticle sorting device 2 in which the control device 1 according to the present technology may be used.
Figure 3:
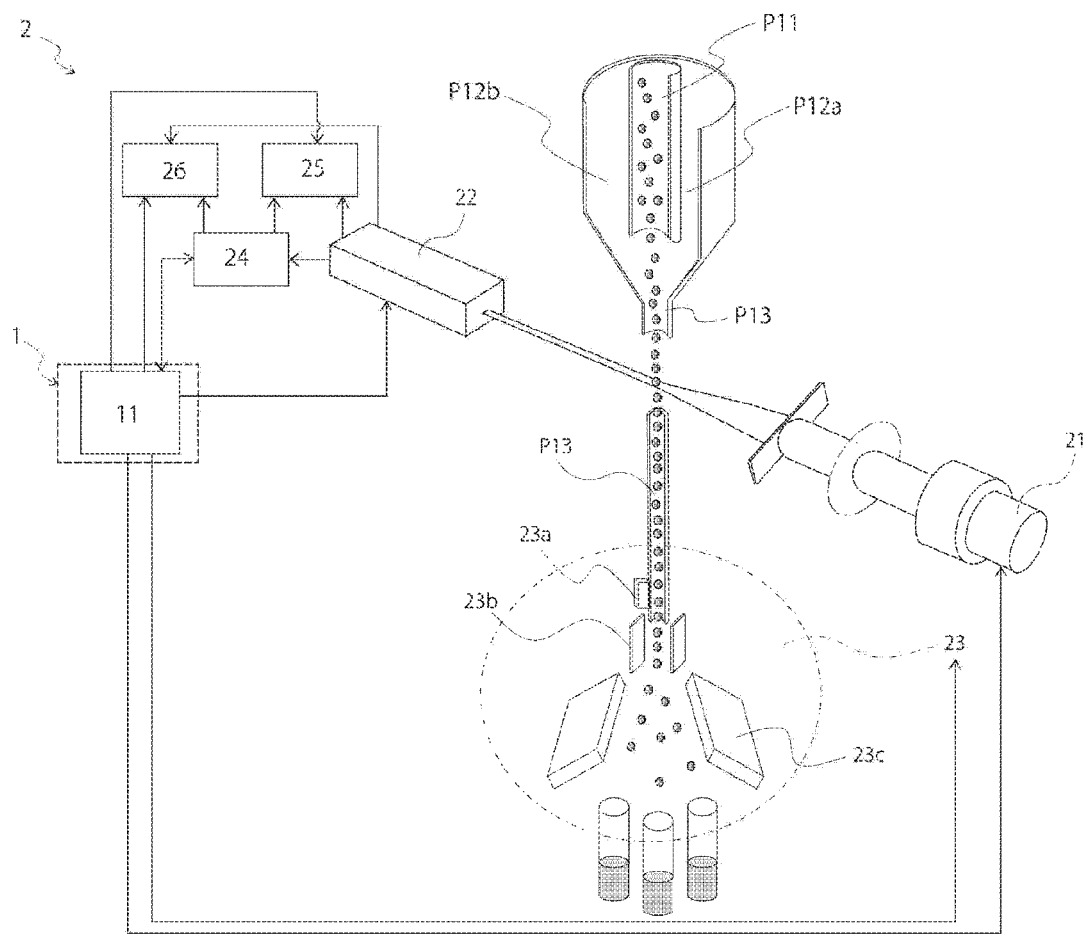
FIG. 3 is a schematic conceptual diagram schematically illustrating a third embodiment of the microparticle sorting device 2 in which the control device 1 according to the present technology may be used.

A control device 1 according to the present technology is a device that controls a processing condition when sorting microparticles from a sample liquid flowing through a flow path P, and includes a control unit 11. FIG. 1 is a schematic conceptual diagram schematically illustrating a first embodiment of a microparticle sorting device 2 in which the control device 1 according to the present technology may be used. FIG. 2 is a schematic conceptual diagram schematically illustrating a second embodiment of the microparticle sorting device 2 in which the control device 1 according to the present technology may be used. FIG. 3 is a schematic conceptual diagram schematically illustrating a third embodiment of the microparticle sorting device 2 in which the control device 1 according to the present technology may be used. The microparticle sorting device 2 according to the present technology at least includes a light detection unit 22, a sorting unit 23, and the control unit 11. Furthermore, the flow path P, a light irradiation unit 21, an analysis unit 24, a storage unit 25, a display unit 26 and the like may be provided as necessary. Hereinafter, each unit is described in detail in time series of sorting.

(1) Flow Path P

In the microparticle sorting device 2 according to the present technology, it is possible to analyze and sort microparticles by detecting optical information obtained from the microparticles arranged in a line in a flow cell (flow path P).

Although the microparticle sorting device 2 may be provided with the flow path P in advance, it is also possible to install a commercially available flow path P, a disposable tip provided with the flow path P and the like in the microparticle sorting device 2 to analyze or sort.

A form of the flow path P is not especially limited, and may be freely designed. For example, this is not limited to the flow path P formed in a two-dimensional or three-dimensional substrate T made by using plastic, glass and the like as illustrated in the first and second embodiments in FIGS. 1 and 2, and the flow path P used in the conventional flow cytometer may also be used in the microparticle sorting device 2 as in the third embodiment illustrated in FIG. 3.

Furthermore, a flow path width, a flow path depth, and a flow path cross-sectional shape of the flow path P are not especially limited as long as a laminar flow may be formed, and may be freely designed. For example, a micro flow path having a flow path width of 1 mm or smaller may also be used in the microparticle sorting device 2. Especially, the micro flow path having the flow path width of about 10 μm or larger and 1 mm or smaller is more preferably used in the microparticle sorting device 2 according to the present technology.

A method of feeding the microparticles is not especially limited, and they may flow in the flow path P depending on the form of the used flow path P. For example, a case of the flow path P formed in the substrate T illustrated in FIGS. 1 and 2 is described. A sample liquid containing the microparticles is introduced into a sample liquid flow path P11, and a sheath liquid is introduced into two sheath liquid flow paths P12a and P12b, respectively. The sample liquid flow path P11 and the sheath liquid flow paths P12a and P12b merge to form a main flow path P13. A sample liquid laminar flow fed in the sample liquid flow path P11 and a sheath liquid laminar flow fed in the sheath liquid flow paths P12a and P12b may merge in the main flow path P13 to form a sheath flow in which the sample liquid laminar flow is sandwiched between the sheath liquid laminar flows.

The microparticles that flow through the flow path P may be labeled with one or two or more dyes such as fluorescent dyes. In this case, the fluorescent dyes available in the present technology include, for example, Cascade Blue, Pacific Blue, fluorescein isothiocyanate (FITC), phycoerythrin (PE), propidium iodide (PI), Texas Red (TR), peridinin chlorophyll protein (PerCP), allophycocyanin (APC), 4',6-diamidino-2-phenylindole (DAPI), Cy3, Cy5, Cy7, Brilliant Violet (BV421) and the like.

(2) Light Irradiation Unit 21

The microparticle sorting device 2 according to the present technology may be provided with the light irradiation unit 21.

The light irradiation unit 21 irradiates the microparticles flowing through the flow path P with light. In the microparticle sorting device 2 according to the present technology, the light irradiation unit 21 is not indispensable, and it is also possible to irradiate the microparticles flowing through the flow path P with light by using an external light irradiation device and the like.

A type of the light applied from the light irradiation unit 21 is not especially limited, but in order to surely generate fluorescence or scattered light from the microparticles, light having constant light direction, wavelength, and light intensity is desirable. There may be a laser, an LED and the like as an example. In a case of using the laser, a type thereof is not especially limited, and it is possible to freely combine one or two or more of an argon ion (Ar) laser, a helium-neon (He—Ne) laser, a dye (dye) laser, a krypton (Cr) laser, a semiconductor laser, a solid laser realized by combining the semiconductor laser and a wavelength conversion optical element or the like to use.

(3) Light Detection Unit 22

The light detection unit 22 optically detects the microparticles flowing through the flow path P. As long as the light detection unit 22 available in the present technology may detect optical signals from the microparticles, a specific light detection method is not especially limited, and it is possible to freely select to adopt the light detection method used in the well-known light detector. For example, it is possible to freely combine one or two or more of the light detection methods used in fluorescence measuring instrument, scattered light measuring instrument, transmitted light measuring instrument, reflected light measuring instrument, diffracted light measuring instrument, ultraviolet spectroscopic measuring instrument, infrared spectroscopic measuring instrument, Raman spectroscopic measuring instrument, FRET measuring instrument, FISH measuring instrument and other various spectrum measuring instruments, a PMT array or a photodiode array in which light receiving elements such as PMTs and photodiodes are one-dimensionally arranged, those in which a plurality of independent detection channels such as two-dimensional light receiving elements such as CCD or CMOS is arranged or the like to adopt.

Furthermore, an installation site of the light detection unit 22 in the microparticle sorting device 2 according to the present technology is not especially limited as long as the optical signals from the microparticles may be detected, and may be freely designed. For example, as illustrated in FIGS. 1 to 3, this is preferably arranged on a side opposite to the light irradiation unit 21 across the flow path P. This is because the light irradiation unit 21 and the light detection unit 22 may be arranged in a freer configuration by arranging the light detection unit 22 on the side opposite to the light irradiation unit 21 across the flow path P. Furthermore, for example, since fluorescence is also emitted in a direction different from an incidence direction of the irradiation light, the light detection unit 22 may also be arranged on the same side as the light irradiation unit 21 or on a side at 90 degrees with reference to the flow path P.

(4) Sorting Unit 23

The sorting unit 23 sorts the microparticles on the basis of the optical information detected by the light detection unit 22. For example, the sorting unit 23 may sort the microparticles downstream the flow path P on the basis of an analysis result such as a size, a form, and an internal structure of the microparticles analyzed from the optical information. Hereinafter, a sorting method is described separately in each embodiment.

(4-1) First Embodiment

For example, in the first embodiment illustrated in FIG. 1, three branching flow paths of a sorting flow path P14 and disposing flow paths P15a and P15b are provided downstream the main flow path P13 formed on the substrate T, microparticles to be sorted that are determined to satisfy a predetermined optical characteristic are taken into the sorting flow path P14, and microparticles not to be sorted that are determined not to satisfy a predetermined optical characteristic are not taken into the sorting flow path P14 and flow to any one of the two disposing flow paths P15a and P15b to be sorted.

The microparticles to be sorted may be taken into the sorting flow path P14 by using a well-known method; for example, by generating a negative pressure in the sorting flow path P14 by a vibration element 23a such as a piezo element and sucking the sample liquid containing the microparticles to be sorted and the sheath liquid into the sorting flow path P14 by utilizing the negative pressure. Furthermore, although not illustrated, it is also possible to take the microparticles to be sorted into the sorting flow path P14 by controlling or changing a laminar flow direction by using a valve electromagnetic force, a fluid stream (gas or liquid) or the like.

In the first embodiment, as illustrated in the schematic conceptual diagram in FIG. 1, by connecting a sample liquid storage unit B1 to the sample liquid flow path P11, a sheath liquid storage unit B2 to the sheath liquid flow paths P12a and P12b, a sorted liquid storage unit B3 to the sorting flow path P14, and waste liquid storage units B4a and Bob to the disposing flow paths P15a and P15b in a communicating manner, a completely closed sorting device may be realized. For example, in a case where the microparticles to be sorted are cells and the like for use in a cell preparation and the like, in order to maintain a sterilized environment and prevent contamination, a completely closed type design (separated from an external environment) as in the first embodiment is preferable.

(4-2) Second Embodiment, Third Embodiment

In the second and third embodiments, for example, by using the vibration element 23a and the like that vibrates at a predetermined vibration frequency to apply vibration to an entire main flow path P13 or a part thereof, a droplet is generated from a discharge port of the main flow path P13. Note that, in this case, the vibration element 23a to be used is not especially limited, and any well-known one may be freely selected and used. As an example, there may be a piezo vibration element and the like. Furthermore, by adjusting a liquid sending amount to the sample liquid flow path P11, the sheath liquid flow paths P12a and P12b, and the main flow path P13, a diameter of the discharge port, the vibration frequency of the vibration element and the like, it is possible to adjust a size of the droplet and generate the droplet containing a constant amount of microparticles.

Next, the droplet is charged with positive or negative charge on the basis of the analysis result such as the size, form, and internal structure of the microparticles analyzed on the basis of the optical information detected by the light detection unit 22 (refer to reference sign 23b in FIGS. 2 and 3). Then, the charged droplet a pathway of which is changed in a desired direction by an opposite electrode 23c to which voltage is applied is sorted.

(5) Control Unit 11

The control unit 11 controls a sorting processing condition in the sorting unit 23. Examples of the sorting processing condition include a flow rate of the sample liquid (driving speed of the sorting unit 23), a sorting processing time, a sorting processing interval and the like, and the control unit 11 may control one or two or more types of conditions.

(5-1) Control Based on Content

The control unit 11 may control the sorting processing condition in the sorting unit 23 on the basis of a content of the microparticles to be sorted in the sample liquid.

For example, at a processing step of autologous cells used in cell therapy such as chimeric antigen receptor (CAR) T cell therapy, there is a demand of learning in detail a proportion of immune cells before sorting and thereafter making a choice to adjust the proportion after the sorting from the viewpoint of improving drug efficacy, reducing side effects, standardizing, and the like. However, for example, a proportion of each immunocompetent cell in the whole blood or in peripheral blood mononuclear cell suspension obtained by utilizing a specific gravity difference therefrom is patient-dependent. Furthermore, this may vary depending on a state at the time of blood collection in some cases. Therefore, in the present technology, by controlling the sorting processing condition in the sorting unit 23 on the basis of the content of the microparticles to be sorted in the sample liquid, it is possible to uniformize the content of target microparticles in a final recovered product even though a content rate of the microparticles to be sorted and the total amount of the sample solution are different for each sample solution to be used.

In a case where the content of the microparticles to be sorted in the sample liquid is not known in advance, a method of measuring the content is not especially limited, and a well-known method capable of measuring the content of the microparticles in the sample liquid may be freely used. In the present technology, by performing a pre-measurement step prior to an actual sorting step by using the microparticle sorting device 2 according to the present technology, it is possible to calculate the content of the microparticles from a measurement result obtained from the sample liquid at the pre-measurement step.

More specifically, as the pre-measurement step, a part of the sample solution is allowed to flow through the flow path P, and the optical information thereof is detected by the light detection unit 22. On the basis of the detected optical information, for example, by performing analysis by using the analysis unit 24 and the like to be described later, it is possible to calculate the content of the microparticles to be sorted in the sample solution.

Note that, in a case where there is a plurality of types of microparticles to be sorted, by calculating a ratio of various types of microparticles in the sample solution at the pre-measurement step, and controlling the sorting processing condition in the sorting unit 23 by the control unit 11 on the basis of the ratio, it is not required to perform the pre-measurement step for each type of the microparticles to be sorted, and it is possible to use a result at one pre-measurement step in the sorting processing condition control of the various types of microparticles.

As a specific example, a method of sorting a plurality of types of cells belonging to a plurality of fractions is described. For example, in order to acquire the required number of cells belonging to a k-th cell fraction, the sorting processing condition (for example, sorting processing time and the like) is set on the basis of a cell ratio calculated on the basis of the result at the pre-measurement step, and a valve and the like of the flow path P is switched to take into the sorting flow path P14, thereby performing the sorting operation. After the required number of cells are acquired after the set time, the cells belonging to a next (k+1)-th cell fraction are sorted in a similar manner. This operation is repeated, and after the cell sorting is finished for all the required cell fractions, a valve to a recovery bag (sorted liquid storage unit B3) is closed to finish the cell sorting step. In this manner, the cells belonging to the respective cell fractions may be sequentially sorted for each cell fraction.

Furthermore, in a case where a plurality of types of cells belonging to a plurality of fractions is collectively sorted into the same sorted liquid storage unit B3 at a predetermined ratio, or, although not illustrated, in a case where the flow path P provided with a plurality of sorting flow paths P14 for the respective cell fractions is used, it is also possible to simultaneously perform the sorting operation of the cells belonging to the respective cell fractions. For example, by setting the sorting processing condition for each cell fraction and performing the sorting operation until the number of sorted cells in each cell fraction reaches the required number of cells, and/or until a ratio of the number of sorted cells in each cell fraction reaches a predetermined ratio, it is also possible to simultaneously sort the cells belonging to the respective cell fractions instead of sorting the same in order for each cell fraction.

The sorting methods may be combined as needed. For example, it is possible to perform the sorting operation in order for each cell fraction at an initial stage of sorting and switch the sorting operation of the cells belonging to the respective cell fractions to the simultaneous method when it reaches a certain number of cells.

(5-2) Control Based on Surviving Rate and/or Activation Rate

In a case where the sorting target is bio-related microparticles, the control unit 11 may also control the sorting processing condition on the basis of a surviving rate and/or an activation rate of the bio-related microparticles to be sorted with respect to the sorting processing condition.

For example, it is general that the considerable number of cells is required as the cells used for cell therapy (for example, $10^7$ or more). For this purpose, it is required that a highly accurate cell sorting operation may be executed at a considerable effective rate (cell recovery rate). In contrast, the cells for cell therapy must sufficiently survive and maintain their activity also at a subsequent gene transfer step and culture step, and finally, they must maintain functions such as tumor responsiveness, too, for example. That is, the cell surviving rate or cell activation rate after sorting is also a very important index at the cell sorting step. Therefore, in the present technology, it is possible to satisfy both the effective rate (microparticle recovery rate) and effective bio-related microparticle recovery by controlling the sorting processing condition on the basis of the surviving rate and/or activation rate of the bio-related microparticles to be sorted with respect to the sorting processing condition.

Figure 4:
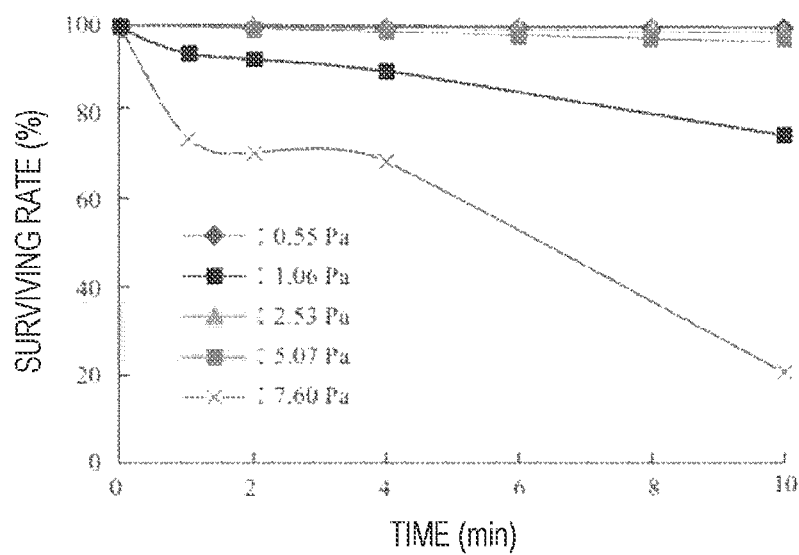
FIG. 4 is a drawing-substituting graph illustrating an effect of a shear stress on a cell surviving rate.
Figure 5:
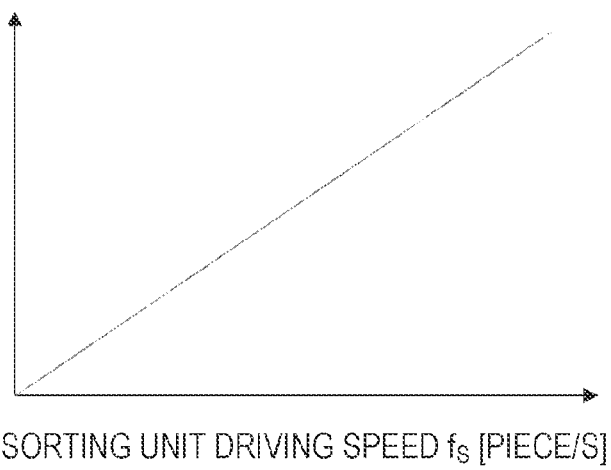
FIG. 5 is a drawing-substituting graph illustrating a relationship between a driving speed of a sorting unit and the shear stress acting on cells.
Figure 6:
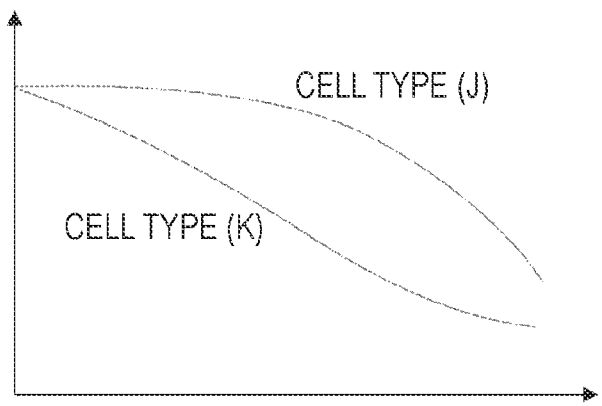
FIG. 6 is a drawing-substituting graph illustrating a relationship between the cell surviving rate and the driving speed of the sorting unit.

A control method based on the surviving rate and/or activation rate of the bio-related microparticles to be sorted with respect to the sorting processing condition is described with more specific examples. For example, the cell surviving rate is known to depend on a shear stress acting on the cells (refer to FIG. 4). FIG. 4 is a drawing-substituting graph illustrating an effect of the shear stress on the cell surviving rate. The shear stress acting on the cells is determined by a flow field in a site where the cells flow when a passage channel is sufficiently large as compared to the cells, and linearly increases according to the flow rate of the sample liquid under the laminar flow (refer to FIG. 5). FIG. 5 is a drawing-substituting graph illustrating a relationship between a driving speed of the sorting unit and the shear stress acting on the cells. Note that, the driving speed of the sorting unit is herein used as an index indicating the flow rate of the sample liquid. As described above, the cell surviving rate depends on the shear stress acting on the cells, that is this also depends on the flow rate of the sample liquid (sorting unit driving speed) (refer to FIG. 6). FIG. 6 is a drawing-substituting graph illustrating a relationship between the cell surviving rate and the driving speed of the sorting unit.

Figure 7:
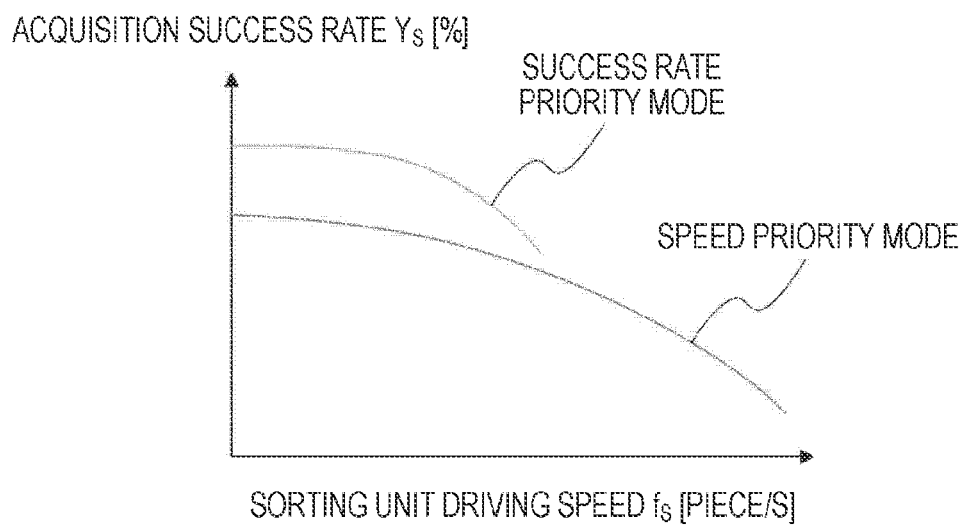
FIG. 7 is a drawing-substituting graph illustrating a relationship between the driving speed of the sorting unit and a cell acquisition success rate, taking a device having two characteristics as an example.
Figure 8:
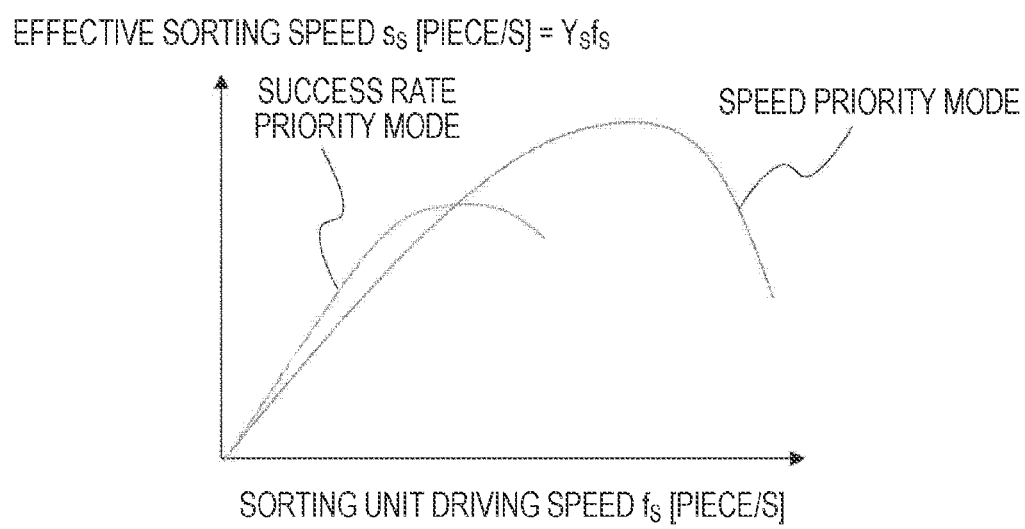
FIG. 8 is a drawing-substituting graph illustrating a relationship between the driving speed of the sorting unit and an effective sorting rate.

Furthermore, a cell acquisition success rate in the cell sorting operation depends on the flow rate of the sample liquid (driving speed of the sorting unit), and generally decreases as the driving speed increases (refer to FIG. 7). FIG. 7 is a drawing-substituting graph illustrating a relationship between the driving speed of the sorting unit and the cell acquisition success rate, taking a device having two modes as an example. Then, the effective cell sorting (acquiring) rate (hereinafter referred to as "effective sorting rate") is obtained as a product of the driving speed of the sorting unit and the acquisition success rate (refer to FIG. 8). FIG. 8 is a drawing-substituting graph illustrating a relationship between the driving speed of the sorting unit and the effective sorting rate. In a case of putting much weight on the cell acquisition, it is desirable to increase the effective sorting rate.

Figure 9A:
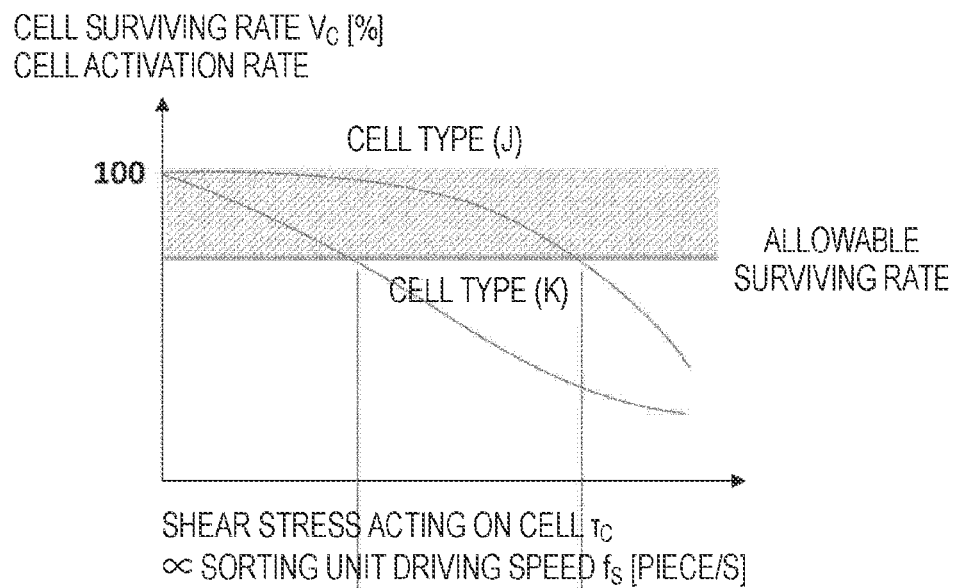
FIGS. 9A and 9B are drawing-substituting graphs illustrating an example in which, when a cell surviving rate lower limit is set with priority, a mode is selected and the sorting unit driving speed is determined, and an acquisition time is determined after setting a driving condition such that the effective sorting rate is maximum under the condition to perform a process.
Figure 9B:
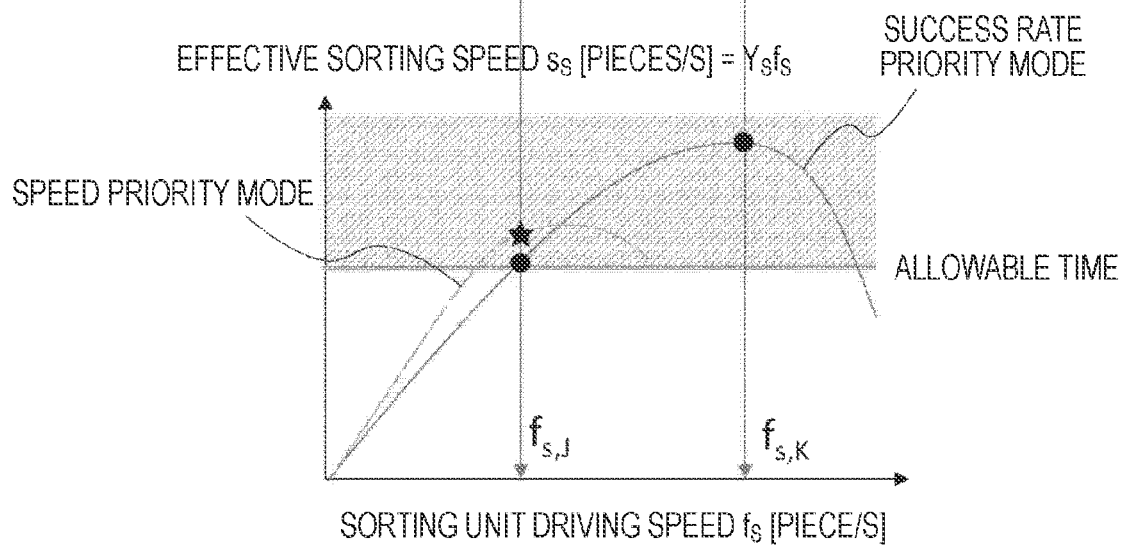

For example, by setting an allowable surviving rate of cells after the sorting as illustrated in FIG. 9A, it is possible to obtain the sorting unit driving speeds that may be set for cell type J and K. As illustrated in FIG. 9B, it may be understood that both a success rate priority mode and a speed priority mode may be used for the cell type K, but only the speed priority mode may be used for the cell type J. Therefore, in a case where only one type of mode may be used, the speed priority mode is used. By using the speed priority mode, driving conditions (flow rate, frequency and the like) are set such that a driving speed $f_{S,K}$ is realized, and a time $N_K/S_S$ to sort the required number of cells $N_K$ is obtained. As indicated by black circles in FIG. 9B, it may be understood that both the cell types J and K are in the allowable time. On the other hand, in a case of a device configuration capable of switching to each mode, switching is performed according to the cell type, and in a case of a device configuration capable of using a plurality of devices, each device is set to a different mode, and the most suitable device may be selected according to the cell type. With such a device configuration, a total acquisition time may be reduced by using the success rate priority mode for the cell type K (refer to a star mark in FIG. 9B).

Note that in the above-described example, the allowable surviving rate is handled as a priority condition, but it is of course possible to control the sorting processing condition by weighting the total acquisition time and the surviving rate and incorporating them into an objective function, and optimizing the same, for example. As for thresholds of the allowable surviving rate, the total acquisition time and the like, values set in advance may be used, or the user may set the same each time according to a purpose and the like.

In a case where the surviving rate and/or activation rate of the bio-related microparticles to be sorted with respect to the sorting processing condition is not known in advance, a method of calculating the surviving rate and/or activation rate is not especially limited, and a well-known method capable of calculating the surviving rate and/or activation rate of the microparticles in the sample liquid may be freely used. In the present technology, by performing the pre-measurement step prior to the actual sorting step by using the microparticle sorting device 2 according to the present technology, it is also possible to calculate the surviving rate and/or activation rate of the bio-related microparticles to be sorted with respect to the sorting processing condition from the measurement result obtained from the sample liquid at the pre-measurement step.

More specifically, as the pre-measurement step, a part of the sample solution is allowed to flow through the flow path P, and the optical information thereof is detected by the light detection unit 22. On the basis of the detected optical information, for example, by performing an analysis by using the analysis unit 24 and the like to be described later, it is possible to calculate the surviving rate and/or activation rate of the bio-related microparticles to be sorted with respect to the sorting processing condition.

On the other hand, in a case where the surviving rate and/or activation rate of the bio-related microparticles to be sorted with respect to the sorting processing condition is known in advance, they may be stored in advance in the storage unit 25 to be described later to be used, or may be received from a database through a network to be used.

Furthermore, it is also possible to store the surviving rate and/or activation rate of the bio-related microparticles to be sorted with respect to the sorting processing condition calculated from the measurement result obtained from the sample liquid at the pre-measurement step in the storage unit 25 to be described later or the database on the network to be used in next or subsequent sorting or sorting of another user.

(5-3) Other Control

In addition to the control of the sorting processing condition in the sorting unit 23, the control unit 11 may also perform various controls for each unit in a manner similar to that of a general microparticle sorting device. For example, it is possible to control a light irradiation condition of the light irradiation unit 21, a light detection condition of the light detection unit 22, an analysis processing condition of the analysis unit 24 and the like.

(6) Analysis Unit 24

The microparticle sorting device 2 according to the present technology may further be provided with the analysis unit 24 as needed. The analysis unit 24 is connected to the light detection unit 22 and analyzes the optical information detected from the microparticles by the light detection unit 22.

For example, the analysis unit 24 calculates a feature amount of each microparticle from the optical information of light received from the light detection unit 22. Specifically, the feature amount indicating the size, form, internal structure and the like of the microparticles is calculated from detected values of received fluorescence and scattered light.

Note that the analysis unit 24 is not indispensable in the microparticle sorting device 2 according to the present technology, and it is also possible to analyze the state and the like of the microparticles by using an external analysis device and the like on the basis of the optical information detected by the light detection unit 22. For example, the analysis unit 24 may be implemented by a personal computer or a CPU, and may be stored as a program in a hardware resource provided with a recording medium (for example, non-volatile memory (USB memory), HDD, CD and the like) and the like and allowed to function by the personal computer or CPU. Furthermore, the analysis unit 24 may be connected to each unit of the microparticle sorting device 2 via a network.

(7) Storage Unit 25

The microparticle sorting device 2 according to the present technology may further be provided with the storage unit 25 in which various data are stored. The storage unit 25, for example, may store all the matters regarding the measurement such as the optical information of the microparticles detected by the light detection unit 22, the sorting processing condition controlled by the control unit 11, and the analysis result analyzed by the analysis unit 24.

Note that in the microparticle sorting device 2 according to the present technology, the storage unit 25 is not indispensable, and it is also possible to store the various data by using an external storage device and the like.

(8) Display Unit 26

The microparticle measuring device 2 according to the present technology may be provided with the display unit 26 that displays various types of information. The display unit 26 may display all the matters regarding the measurement such as the optical information of the microparticles detected by the light detection unit 22, the sorting processing condition controlled by the control unit 11, and the analysis result analyzed by the analysis unit 24.

In the microparticle measuring device 2 according to the present technology, the display unit 26 is not indispensable, and an external display device may also be connected. As the display unit 26, for example, a display, a printer and the like may be used.

2. Microparticle Sorting System 3

Figure 10:
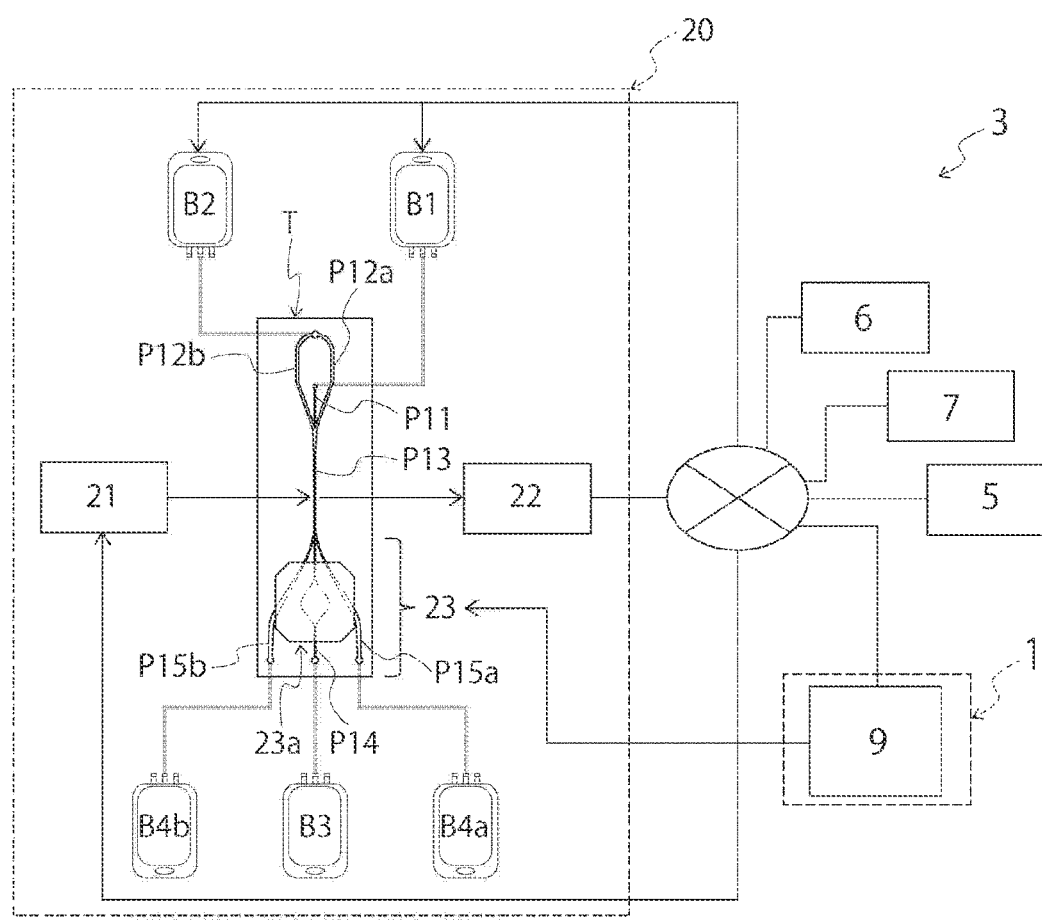
FIG. 10 is a schematic conceptual diagram schematically illustrating an embodiment of a microparticle sorting system 3 according to the present technology.

FIG. 10 is a schematic conceptual diagram schematically illustrating an embodiment of a microparticle sorting system 3 according to the present technology. The microparticle sorting system 3 according to the present technology includes a sorting device 20 provided with a light detection unit 22 and a sorting unit 23, and a control device 1 provided with a control unit 11.

Furthermore, the flow path P, a light irradiation unit 21, an analysis unit 24, a storage unit 25, a display unit 26 and the like may be provided as necessary. They may be provided in the sorting device 20 and the control device 1, or may be arranged independently. For example, the sorting device 20 may be provided with the flow path P in advance, but it is also possible to install a commercially available flow path P, a disposable tip provided with the flow path P and the like on the sorting device 2 to analyze or sort. Furthermore, although the light irradiation unit 21 may be provided on the sorting device 20 in advance, it is also possible to irradiate microparticles flowing through the flow path P with light by using an external light irradiation device and the like. Moreover, the analysis unit 24, the storage unit 25, and the display unit 26 may be provided in the sorting device 20 or the control device 1 in advance, but external analysis device, storage device, display device and the like may also be used. In this case, each device may be connected via a network.

Note that since the details of each unit are the same as the details of each unit of the control device 1 and the microparticle sorting device 2 according to the present technology described above, the description thereof is herein omitted.

3. Control Method, Microparticle Sorting Method

A control method according to the present technology is a method of controlling a processing condition when sorting microparticles from a sample liquid flowing through a flow path P, and includes a control step. A microparticle sorting method according to the present technology includes at least a light detection step, a sorting step, and a control step. Furthermore, as necessary, a flowing step, a light irradiation step, an analysis step, a storage step, a display step and the like may also be performed. Note that since the details of each step are the same as those of a step performed by each unit of the microparticle sorting device 2 according to the present technology described above, the description thereof is herein omitted.

Figure 11:
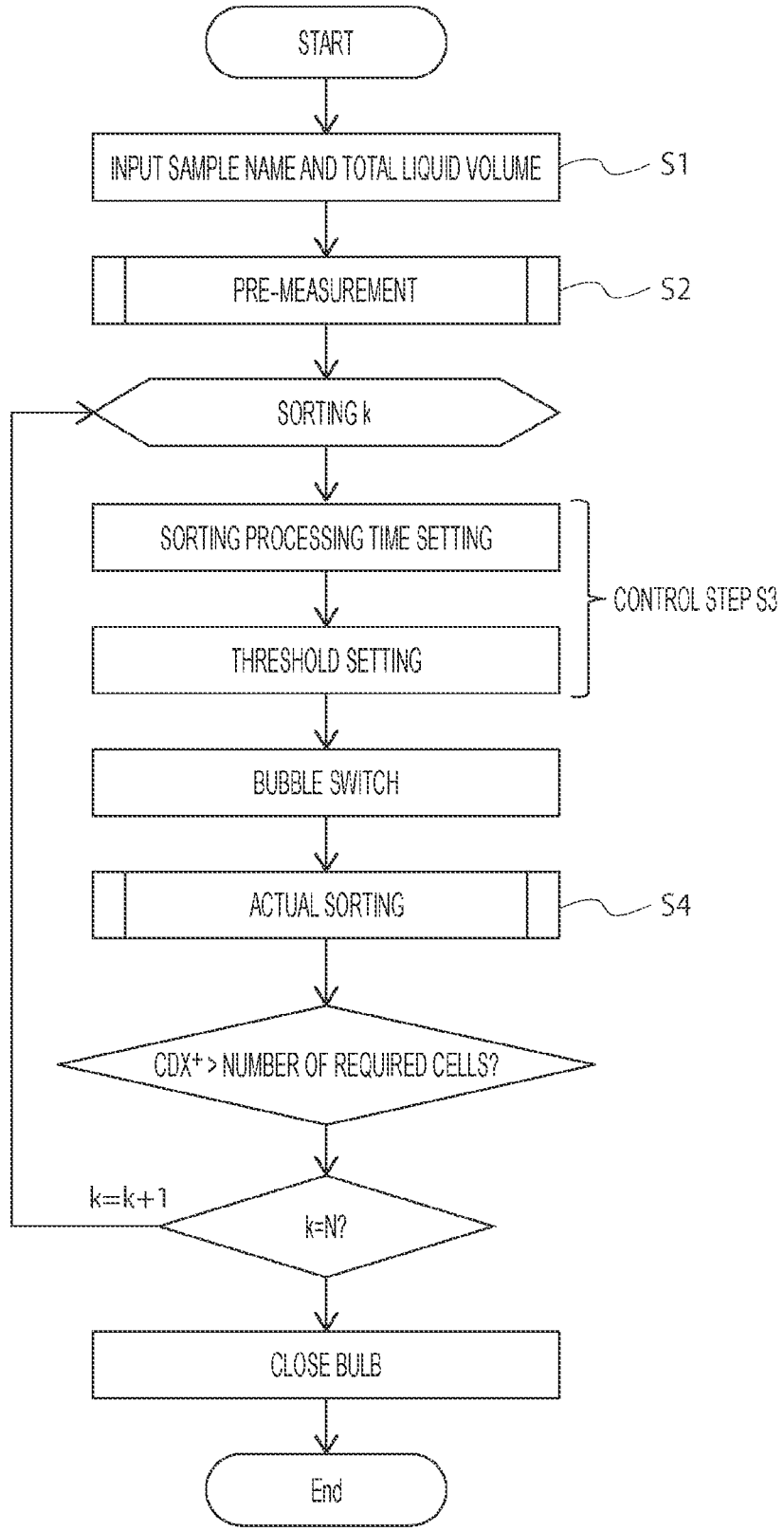
FIG. 11 is a flowchart of an embodiment of a microparticle sorting method using a control method according to the present technology.
Figure 12:
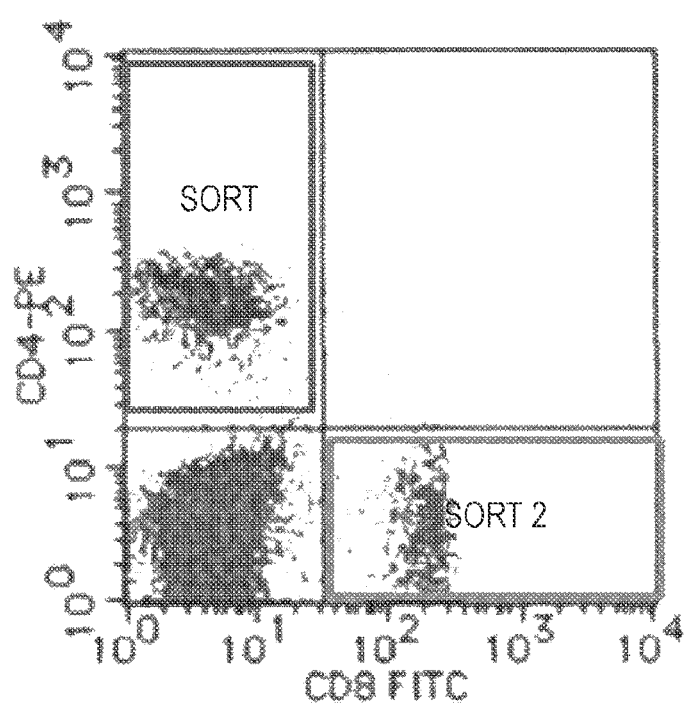
FIG. 12 is a drawing-substituting graph illustrating an example of a results obtained by pre-measurement.

FIG. 11 is a flowchart of an embodiment of the microparticle sorting method using the control method according to the present technology. This embodiment is an example in which $CD4^+T$ cells and $CD8^+T$ cells are acquired from samples derived from different patients at a ratio of 1:1. First, a biological sample collected from the patient is subjected to pretreatment such as centrifugation and chemical treatment, then various types of information (sample name, total liquid volume and the like) are input to the microparticle sorting device to be used (S1), and pre-measurement step S2 to determine a ratio of $CD4^+T$ cells and $CD8^+T$ cells is performed. At the pre-measurement step S2, the flowing step, the light irradiation step, the analysis step, the storage step, the display step and the like are performed. An example of a result obtained at the pre-measurement step S2 is illustrated in FIG. 12. On the basis of the result illustrated in a graph in FIG. 12, at control step S3, for example, a threshold of a cell sorted amount is set.

Next, the sorting processing condition (for example, sorting processing time, threshold of sorted amount and the like) is set on the basis of a cell ratio calculated on the basis of the result of the pre-measurement step (control step S3), a valve and the like of the flow path P is switched, and actual sorting is performed (S4). At actual sorting step S4, as at pre-measurement step S2, the flowing step, the light irradiation step, the analysis step, the storage step, the display step and the like are performed. After the required number of cells are acquired after the set time, the cells belonging to a next (k+1)-th cell fraction are sorted in a similar manner. This operation is repeated, and after the cell sorting is finished for all the required cell fractions, a valve to a recovery bag is closed to finish the cell sorting step.

The example of the result of acquiring the $CD4^+T$ cells and $CD8^+T$ cells at a ratio of 1:1 from the samples derived from the different patients by using this embodiment is illustrated in following Table 1. As illustrated in Table 1, even if a content rate of the microparticles to be sorted and the total amount of the sample solution are different for each sample solution to be used, a content of the target microparticles in a final recovered product may be made uniform.

TABLE 1

| | Relative # cell in Bag | | | |
| --- | --- | --- | --- | --- |
| | Input A | Input B | Output A | Output B |
| CD4+Tcell | 25% | 40% | 49% | 49% |
| CD8+Tcell | 40% | 12% | 49% | 49% |
| Bcell | 15% | 13% | 0% | 0% |
| Nkcell | 10% | 5% | 0% | 0% |
| Other | 10% | 30% | 2% | 2% |
| Total cell # | unknown | unknown | $1 \times 10^7$ cells | $1 \times 10^7$ cells |
| Volume | 200 mL | 185 mL | 50 mL | 50 mL |

4. Control Program

A control program according to the present technology is a program used to control a condition of sorting microparticles from a sample liquid flowing through a flow path, the program for allowing a computer to realize a control function of controlling a sorting processing condition on the basis of a content of microparticles to be sorted in the sample liquid.

The control program according to the present technology is recorded in an appropriate recording medium. Note that since the control function in the control program according to the present technology is the same as the control function performed by the control unit 11 of the control device 1 described above, description thereof is herein omitted.

Note that the present technology may also take the following configuration.

(1)

A control device being a device that controls a processing condition when sorting microparticles from a sample liquid flowing through a flow path, the control device provided with:

a control unit that controls a sorting processing condition on the basis of a content of microparticles to be sorted in the sample liquid.

(2)

The control device according to (1), in which the content is calculated from a measurement result obtained from the sample liquid at a pre-measurement step.

(3)

The control device according to (1) or (2), in which the sorting processing condition is one or more conditions selected from a flow rate of the sample liquid, a sorting processing time, and a sorting processing interval.

(4)

The control device according to any one of (1) to (3), in which the microparticles are bio-related microparticles.

(5)

The control device according to (4), in which the control unit controls the sorting processing condition on the basis of a surviving rate and/or an activation rate of bio-related microparticles to be sorted with respect to the sorting processing condition.

(6)

The control device according to (5), in which the surviving rate and/or the activation rate is calculated from a measurement result obtained from the bio-related microparticles in the sample liquid at a pre-measurement step.

(7)

A microparticle sorting device provided with:

a light detection unit that detects optical information obtained from a sample liquid;

a sorting unit that sorts microparticles from the sample liquid on the basis of the detected optical information; and a control unit that controls a sorting processing condition in the sorting unit on the basis of a content of microparticles to be sorted in the sample liquid.

(8)

A microparticle sorting system provided with:

a sorting device provided with a light detection unit that detects optical information obtained from a sample liquid flowing through a flow path, and a sorting unit that sorts microparticles from the sample liquid on the basis of the detected optical information; and a control device provided with a control unit that controls a sorting processing condition in the sorting unit on the basis of a content of microparticles to be sorted in the sample liquid.

(9)

A control method being a method of controlling a condition of sorting microparticles from a sample liquid flowing through a flow path, the control method provided with:

a control step of controlling a sorting processing condition on the basis of a content of microparticles to be sorted in the sample liquid.

(10)

A control program being a program used to control a condition of sorting microparticles from a sample liquid flowing through a flow path, the control program for allowing a computer to realize a control function of controlling a sorting processing condition on the basis of a content of microparticles to be sorted in the sample liquid.

REFERENCE SIGNS LIST

1 Control device
2 Microparticle sorting device
P Flow path
21 Light irradiation unit
22 Light detection unit
23 Sorting unit
11 Control unit
24 Analysis unit
25 Storage unit
26 Display unit
3 Microparticle sorting system

The invention claimed is:

1. A control device, comprising:
a control unit configured to control a sorting processing condition to sort a plurality of microparticles from a sample liquid which flows through a flow path, wherein the plurality of microparticles comprises a plurality of bio-related microparticles, and
the control of the sorting processing condition is based on at least one of a surviving rate or an activation rate of the plurality of bio-related microparticles to be sorted with respect to the sorting processing condition.

2. The control device according to claim 1, wherein
the control unit is further configured to control the sorting processing condition based on a content of the plurality of bio-related microparticles, and
the content is calculated based on a result of a measurement process prior to the sorting of the plurality of bio-related microparticles.

3. The control device according to claim 1, wherein the sorting processing condition comprises at least one of a flow rate of the sample liquid, a sorting processing time, or a sorting processing interval.

4. The control device according to claim 1, wherein each of the surviving rate and the activation rate is calculated based on a result of a measurement process prior to the sorting of the plurality of bio-related microparticles in the sample liquid.

5. A microparticle sorting device, comprising:
a light detection unit configured to detect optical information obtained from a sample liquid;
a sorting unit configured to sort a plurality of microparticles from the sample liquid based the detected optical information and a sorting processing condition, wherein the plurality of microparticles comprises a plurality of bio-related microparticles; and
a control unit configured to control the sorting processing condition in the sorting unit based on at least one of a surviving rate or an activation rate of the plurality of bio-related microparticles to be sorted with respect to the sorting processing condition.

6. A microparticle sorting system, comprising:
a sorting device comprising:
a light detection unit configured to detect optical information obtained from a sample liquid that flows through a flow path; and
a sorting unit configured to sort a plurality of microparticles from the sample liquid based the detected optical information and a sorting processing condition, wherein the plurality of microparticles comprises a plurality of bio-related microparticles; and
a control device configured to control the sorting processing condition in the sorting unit based on at least one of a surviving rate or an activation rate of the plurality of bio-related microparticles to be sorted with respect to the sorting processing condition.

7. A control method, comprising:
controlling a sorting processing condition for sorting a plurality of microparticles from a sample liquid flowing through a flow path, wherein
the plurality of microparticles comprises a plurality of bio-related microparticles, and
the control of the sorting processing condition is based on at least one of a surviving rate or an activation rate of the plurality of bio-related microparticles to be sorted with respect to the sorting processing condition.

8. A non-transitory computer-readable medium having stored thereon, computer-executable instructions which, when executed by a computer, cause the computer to execute operations, the operations comprising:
controlling a sorting processing condition for sorting a plurality of microparticles from a sample liquid flowing through a flow path, wherein
the plurality of microparticles comprises a plurality of bio-related microparticles, and
the control of the sorting processing condition is based on at least one of a surviving rate or an activation rate of the plurality of bio-related microparticles to be sorted with respect to the sorting processing condition.

* * * * *